(12) United States Patent
Arterson

(10) Patent No.: US 7,663,128 B2
(45) Date of Patent: Feb. 16, 2010

(54) RADIATION SHIELD SECURING AND COVERING SYSTEM

(76) Inventor: Charles Arterson, 10 Dowling Cir., Apt. - T-2, Parkville, MD (US) 21234

(*) Notice: Subject to any disclaimer, the term of this patent is extended or adjusted under 35 U.S.C. 154(b) by 347 days.

(21) Appl. No.: 11/893,854

(22) Filed: Aug. 18, 2007

(65) Prior Publication Data

US 2009/0045358 A1 Feb. 19, 2009

(51) Int. Cl.
*G21F 3/02* (2006.01)

(52) U.S. Cl. .................. 250/519.1; 250/515.1

(58) Field of Classification Search .......... 250/519.1, 250/516.1, 515.1
See application file for complete search history.

(56) References Cited

U.S. PATENT DOCUMENTS 7,391,042 B2 * 6/2008 Goldstein .......... 250/515.1

* cited by examiner

*Primary Examiner*—Kiet T Nguyen
(74) *Attorney, Agent, or Firm*—Donald W. Meeker

(57) ABSTRACT

A flexible ionizing radiation shield attached to an X-ray machine by a long retractable cable. An elongated opening adjacent to a top edge is used as a hand hold to manipulate the flexible shield during usage and as a means to hang the flexible shield onto two hooks on the cable housing for storage. Sanitary disposable shield covers are dispensed from a dispenser mounted above the shield hanger.

6 Claims, 3 Drawing Sheets

RADIATION SHIELD SECURING AND COVERING SYSTEM

CROSS-REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH OR DEVELOPMENT

Not Applicable.

BACKGROUND OF THE INVENTION

Field of the Invention

The present invention relates to flexible radiation shields and particularly to a flexible ionizing radiation shield for the protection of patients during ionizing radiation exposure, the flexible shield being attached to an X-ray machine component by a long retractable cable in a housing locked onto the X-ray machine component, the flexible shield having an elongated opening adjacent to a top edge for dual usage including a hand hold for manipulating the flexible shield during usage and a means to hang the flexible shield onto the housing by hanging the elongated opening over two adjacent hooks on the housing for storage to insure that the flexible shield is always available for use with the X-ray machine and further comprising sanitary disposable shield covers from a dispenser mounted on an X-ray machine component, the sanitary disposable shield covers used to enclose the shield for each usage to prevent exposure of patients to any infectious disease cross contamination from the flexible shield and to dispose of the shield cover after use. Description of Related Art including information disclosed under 37 CFR 1.97 and 1.98

X-rays are short wave electromagnetic energy sources which can penetrate solid matter, which are commonly used in medicine for diagnostic and therapeutic purposes. While X-rays serve as an important medical diagnostic and therapeutic tool, they are harmful to the living cells and tissues of the patient to whom the X-rays are directed and to the medical personnel who administer the X-rays. Many prior art devices have been made to shield patients or medical personnel from the harmful radiation.

A flexible radiation shield intended for use with a portable or stationary X-ray machine to shield portions of a patient often becomes separated from the X-ray machine and may not be available for use when the patient is being X-rayed thereby endangering parts of the patient normally covered by the shield when being X-rayed. When used, the radiation shields are often just placed over a portion of a patient during an X-ray and then stored and used with each subsequent patient without cleaning or covering the shield so that patients may be exposed to infectious disease contamination from other patients using the shield. Prior art devices do not adequately address these problems.

U.S. Pat. No. 5,379,332, issued Jan. 3, 1995 to Jacobson, concerns a launderable and replaceable lead blanket cover system for rehabilitating contaminated lead blankets. Lead blankets which can be removed from a nuclear facility or which are manufactured directly, include an outer cover which is heat sealed around the periphery to the inner lead blanket. The heat sealed periphery can include a plurality of blanket supporting metal grommets having a uniform predetermined spacing. A contaminated lead blanket which cannot be removed from a nuclear facility, has the contaminated cover removed in the nuclear facility and securing strips are secured to the inner cover. The contaminated lead blanket then is rehabilitated by adding a replaceable cover open on one end and having a heat sealed periphery and metal grommets in the other three sides. The open end with the lead blanket inside is then folded over and sealed, such as with an adhesive and then metal grommets can be secured through the sealed periphery to complete the lead blanket. A replaceable cover lead blanket can also be initially formed, if desired. Utilized with either type of lead blanket embodiment is a launderable and incinerable outer cover. The launderable cover includes two piece securing grommets having the same spacing as the metal grommets. The pieces are snapped together through the metal grommets to secure the launderable cover to the lead blanket and unsnapped to remove the cover for laundering or incineration.

U.S. Pat. No. 6,974,961, issued Dec. 13, 2005 to George, illustrates a disposable cover for electromagnetic treatment applicators that prevents undesired exposure to potentially harmful radiation. The cover is a pouch-like structure having a back surface (which faces opposite, or away from, the treatment area) constructed from shielding material, such as metallized polyethylene. At least a portion of the cover which faces the treatment area is constructed solely from non-shielding material. Adhesive strips, ZIP-LOCK.®, or other interlocking edges, secure the applicator inside the cover and close off any leaks. The electromagnetic properties of the cover are integrated into the circuitry for the treatment applicator, such that the applicator is not functional in the absence of the cover. In use, an electromagnetic treatment applicator is inserted into the cover and positioned over the area to be treated, with the non-shielding, or "window", portion of the cover overlying the treatment area. Once assembled, the applicator/cover combination forms a closely matched and tuned network for effecting a highly efficient RF output. When activated, the generated electromagnetic energy only exits the cover through the opening or "window", thereby preventing exposure of the patient or caregiver to potentially harmful radiation.

U.S. Pat. No. 5,523,581, issued Jun. 4, 1996 to Cadwalader, puts forth a slipcover or covering for containing a flexible radiation shield that allows the radiation shield to be reused without experiencing staining. The slipcover may be configured to cover the thyroid area, male gonadal areas, female gonadal areas, breast area, hands, and eyes. The radiation shield includes a radiation attenuating material and is inserted within a pocket or pouch in the slipcover. The slipcover includes a fastener for selectively opening and closing the pocket. The slipcover is preferably made of a surgical drape material such as a wood pulp or polyester material. The radiation shield may be coated in a fabric material to ease placement and removal of the radiation shield into and out of the pocket.

U.S. Pat. No. 4,062,518, issued Dec. 13, 1977 to Stivender, discloses a diagnostic X-ray table, a first group of X-ray shielding panels are supported for rotation on a carrier and another group of panels are supported on a lever that is pivotally connected to the carrier. The lever may be aligned with the carrier to present the combined width of all panels across the front of a combination spot film and fluoroscopic device. Means responsive to pivoting the lever along the side of the apparatus rotate the first group of panels to substantial parallelism with second group to present the panels along the side of the apparatus when the spot film and fluoroscope device is angulated to put the patient being examined in an erect posture.

U.S. Pat. No. 5,417,225, issued May 23, 1995 to Rubenstein, claims a radiation shield including an aperture connected to an edge of the shield by a slit, which is held closed by a releasable flap. Instrumentation can be inserted through the aperture to contact a patient over which the shield is draped. By releasing the flap and thereby opening the aperture toward the edge of the shield, the shield can be removed from the patient without removing the instrumentation inserted through the aperture. A secondary shield is releasably secured over the aperture, affording further protection. Because the shield is placed within the septic field during use, the shield includes a sterilizable or disposable outer covering.

U.S. Pat. No. 3,967,129, issued Jun. 29, 1976 to Winkler, indicates a radiation shield in the form of a stranded curtain made up of bead-chains whose material and geometry are selected to produce a cross-sectional density that is the equivalent of 0.25 mm or more of lead and which curtain may be mounted on various radiological devices to shield against scattered radiation while offering a minimum of obstruction to the radiologist.

U.S. Pat. No. 2,794,128, issued May 28, 1957 to Shasky, is for an "X-Ray Shield", wherein the X-ray machine has a mounting plate with a plurality of clips attached thereto at one edge thereof. A shield of flexible opaque radiant material is affixed to the clips.

U.S. Pat. No. 7,099,427, issued Aug. 29, 2006 to Cadwalader, provides a radiation attenuation system for use with Computed Tomography procedures. The system includes a shield made of a radiation attenuation material and may be useful in blocking or attenuating radiation, and assisting in the protection of at least one of a patient and a medical personnel present during the Computed Tomography procedure. The system may be useful for both Computed Tomography scanning procedures and Computed Tomography fluoroscopy procedures. FIGS. 4 and 5, show a shielding drape attached to the table and to the CT machine by means of hook and loop fasteners in addition to hook and loop fasteners, snaps, grommets, adhesives, or zippers, etc. This device is not retractably mounted to the CT machine.

U.S. Pat. No. 6,674,087, issued Jan. 6, 2004 to Cadwalader, shows a radiation attenuation system including a polymeric resin comprising a web. The system also includes a radiation attenuation material dispersed at least partially in the web. The system has a radiation transmission attenuation factor of at least about 10% of a primary 100 kVp X-ray beam. A method of making a radiation attenuation system including a radiation attenuation material dispersed at least partially in a polymeric resin is also disclosed. The method includes extruding the radiation attenuation material and the polymeric resin thereby forming an extrusion. The method also includes forming the extrusion into a web. The web has a radiation transmission attenuation factor of at least about 10% of a primary 100 kVp X-ray beam. A shield for the attenuation of radiation is also disclosed. The shield may be disposable or may be sterilized between uses.

U.S. Pat. No. 6,325,538, issued Dec. 4, 2001 to Heesch, describes a radiation field isolator shield apparatus that encloses the human torso (or part of a human torso) during X-ray procedures. The shield protects medical personnel from scatter radiation, is adjustable to fit different size torsos, and will move with the X-ray equipment as the position of the equipment is adjusted to examine different areas of the body.

What is needed is a retractable cable for securing a radiation shield to a portable or stationary X-ray machine component to prevent loss of the shield. To insure the additional safety of each patient being X-rayed a new disposable plastic bag is used on each patent to encase the X-ray shield during use on a patient, so that the health of the patient is further protected by being shielded from infection disease cross contamination from other patients using the X-ray shield.

BRIEF SUMMARY OF THE INVENTION

An object of the present invention is to provide a retractable cable for securing a radiation shield to a portable or stationary X-ray machine component. The cable prevents the loss of the shield and insures the shields availability at all times. Disposable plastic shield covers are pulled from a dispenser on an X-ray machine component to encase the radiation shield during use on a patient, so that the health of the patient is further protected by being shielded from cross contamination of infectious diseases from other patients using the X-ray shield. The present invention achieves radiation protection and infection control, and keeps the shield consistently available and ready to use thereby improving the overall quality of patient care and meeting standard precautions safety performance compliance because the shield will always be with the X-ray machine equipment to be ready for any random unannounced accreditation compliance survey.

In brief, the radiation shield securing and covering system of the present invention comprises a flexible lead-impregnated or other type of ionizing radiation shield for the protection of patients during ionizing radiation exposure, the flexible shield being attached to an X-ray machine component by a long retractable cable in a cable casing locked onto the X-ray machine component. The flexible shield has an elongated horizontal opening adjacent to a top edge for dual usage including a hand hold for manipulating the flexible shield during usage and a means to hang the flexible shield onto the casing by hanging the elongated opening over two horizontally spaced hooks on the casing for storage to insure that the flexible shield is always available for use with the X-ray machine. The system of the present invention further comprises sanitary disposable shield covers from a dispenser mounted on an X-ray machine component, the sanitary disposable shield covers used to enclose the shield for each usage to prevent exposure of patients to any contamination from the shield and to dispose of the shield cover after use to prevent the spread of communicable diseases between patients using the shield and from handling by technicians.

An advantage of the present invention is that it insures that a patient will be protected from radiation in body areas surrounding the actual part of the body being X-rayed.

Another advantage of the present invention is that it protects the patient from infectious diseases which might spread from other patients if the radiation shield were not covered.

One more advantage of the present invention is that it insures that the radiation shield will always be with the portable or stationary X-ray machine.

BRIEF DESCRIPTION OF THE SEVERAL VIEWS OF THE DRAWINGS

These and other details of my invention will be described in connection with the accompanying drawings, which are furnished only by way of illustration and not in limitation of the invention, and in which drawings.

DETAILED DESCRIPTION OF THE INVENTION

Figure 1:
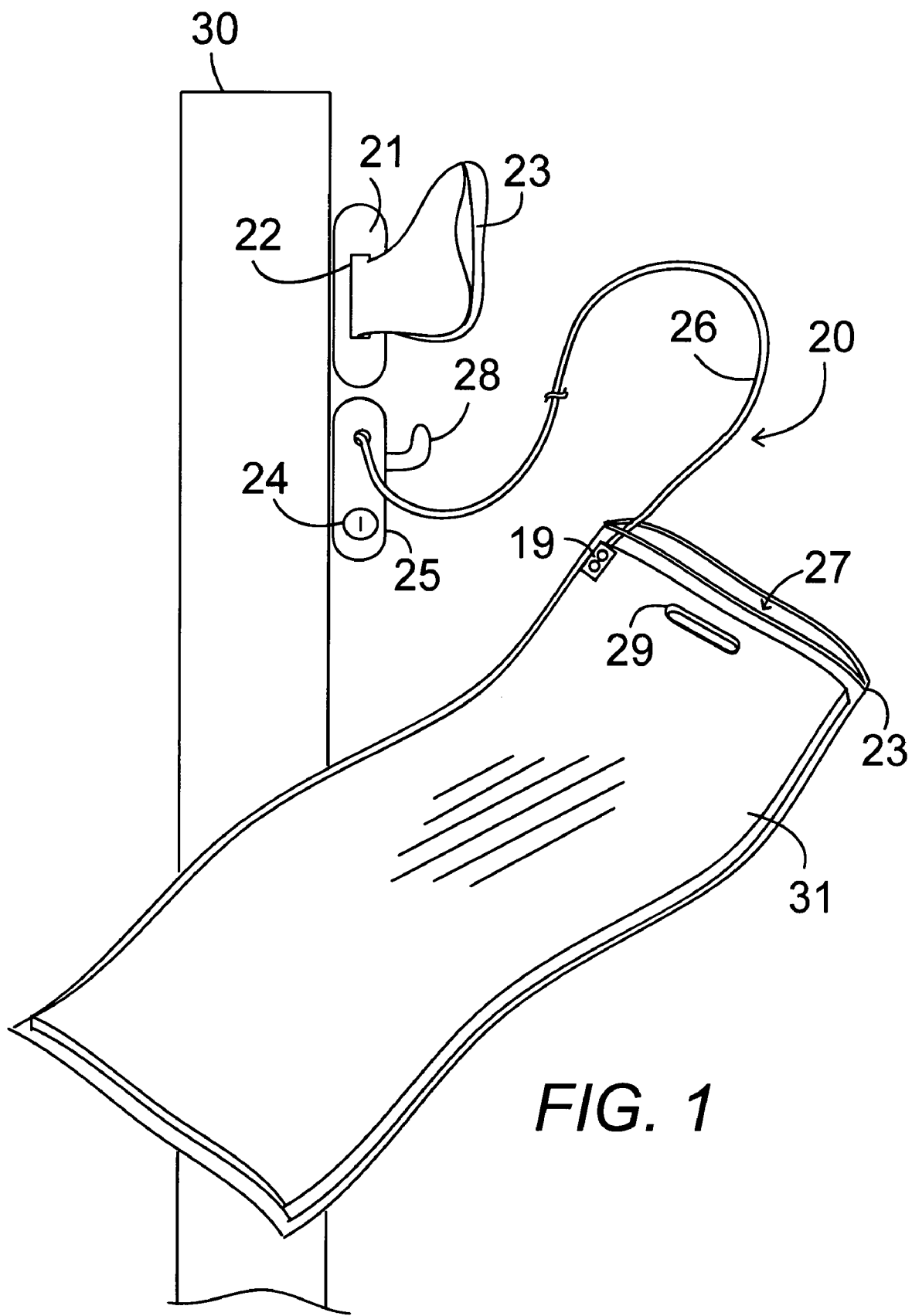
FIG. 1 is a perspective view of the radiation shield securing and covering system of the present invention shown with the radiation shield out for use with a patient and a disposable bag covering the radiation shield.
Figure 2:
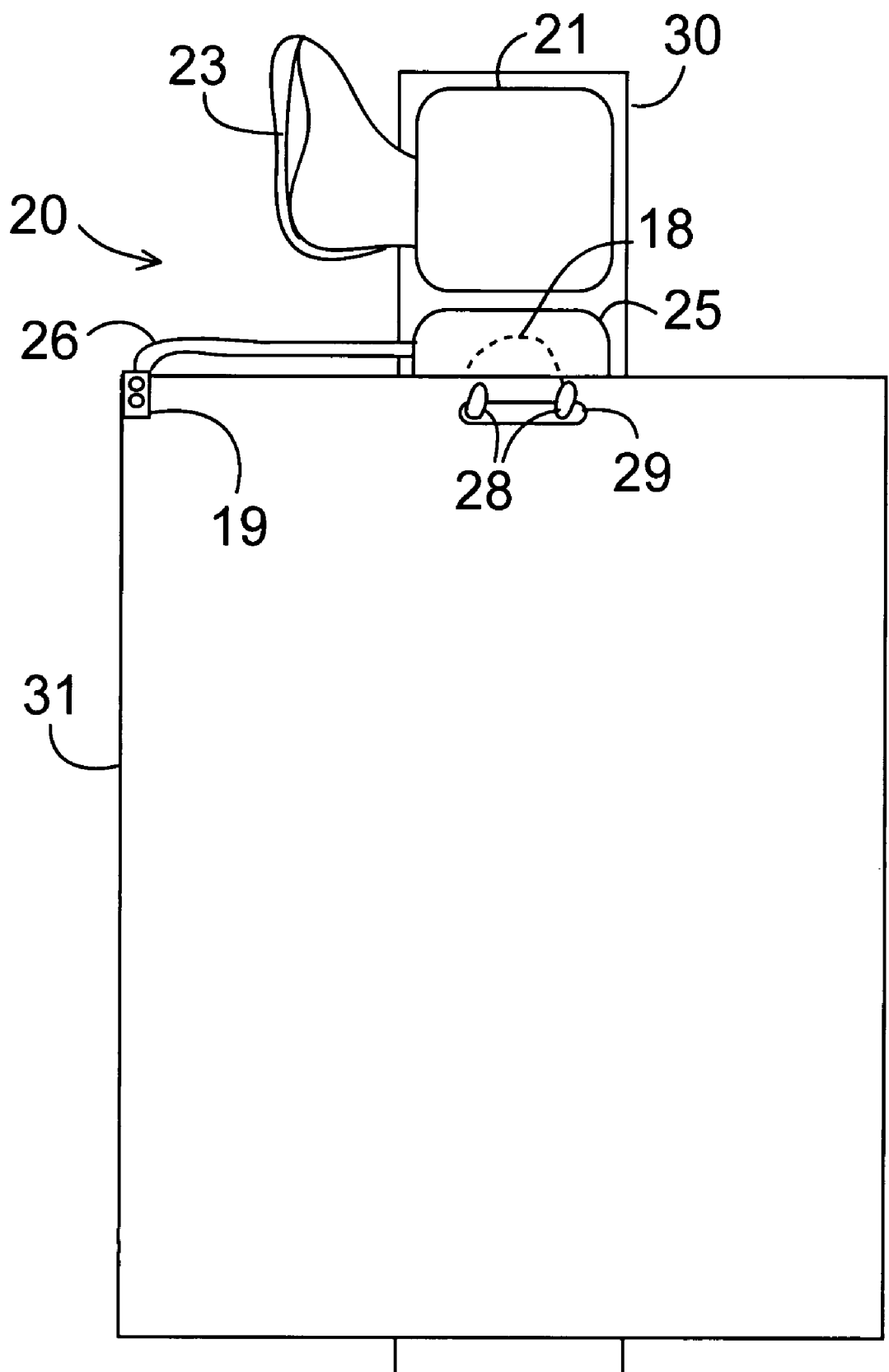
FIG. 2 is a front elevational view of the radiation shield securing and covering system of FIG. 1 shown with the radiation shield hanging on the cable casing hooks on an X-ray machine component.
Figure 3:
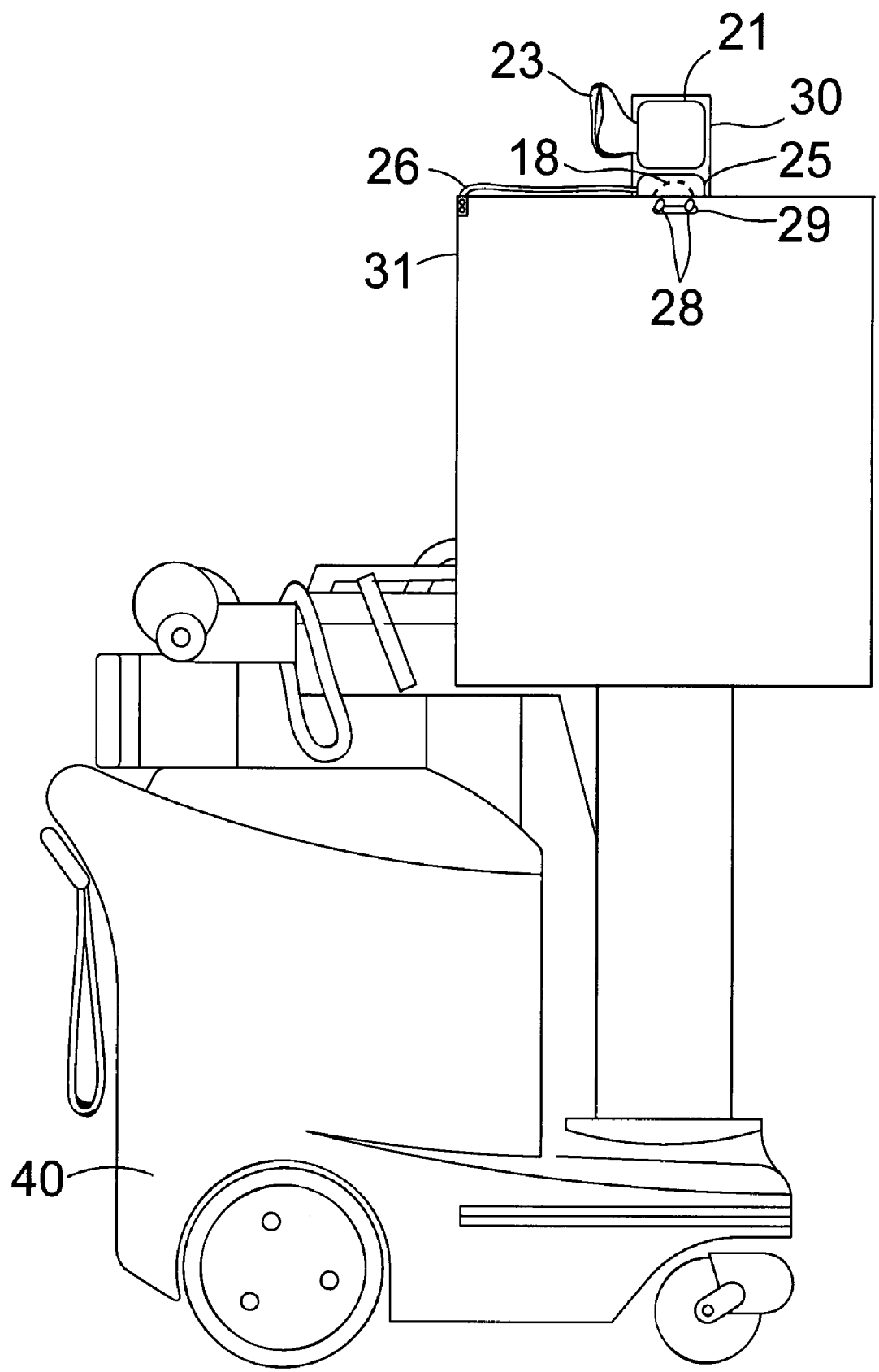
FIG. 3 is a side elevational view of a portable X-ray machine having the radiation shield and disposable bag dispenser of the present invention mounted on the post of the machine.

In FIGS. 1-3, a radiation shield securing and covering system 20 comprises a radiation shield 31 attached by a retractable cable 26 to a cable casing 25 with hooks 28 through a shield hand opening 29 to support the shield stored on a post 30 (tower) or other convenient location on a portable X-ray machine 40 and a dispenser 21 for sanitary disposable bags 23 to cover the shield in use.

The radiation shield 31 comprises a flexible sheet of radiation attenuation material, which may be impregnated with lead shielding, for preventing passage of all ionizing radiation through the shield to protect a patient from all ionizing radiation exposure on areas of the patient covered by the shield. The shield 31 further comprises a means for handling the sheet of material during use with a patient and a means for hanging the material on an X-ray machine component. Preferably, the means for handling the shield and means for hanging the shield comprises an elongated horizontal opening 29 adjacent to a top end of the shield to receive at least one hand of a user during use of the shield with the cable 26 extended, as shown in FIG. 1, and alternately to receive a pair of hooks 28 on the cable casing 25 for hanging the shield 31 on the X-ray machine component, as shown in FIG. 2. Alternately, there may be at least one hook attached to any X-ray machine component for hanging the shield 31 for storage with the X-ray machine or attached on or adjacent to a permanently fixed X-ray machine.

The retractable cable 26 is attached at a first end by a means for permanently securing the cable to a radiation shield, such a plate 19 at the end of the cable attached by rivets or bolts, and at a second end to a retractable spool 18 in the cable casing 25 locked onto an X-ray machine component to insure that the shield is always with the X-ray machine to shield each patient being X-rayed from all ionizing radiation exposure on areas of the patient covered by the shield.

The cable casing 25 comprises a rigid structure having the two hooks 28 horizontally spaced on the casing to fit within the elongated horizontal opening 29 to support the shield 31 hanging on the hooks for storage of the shield. The cable casing 25 houses a spring loaded spool 18 to retract the cable 26 after use of the shield 31. The cable casing 25 preferably further comprises a means for locking the cable casing onto the X-ray machine component, which may be an integrated lock with a keyhole 24 on the outside of the casing or the casing 25 may be secured by a strong permanent adhesive or by welding or other secure attaching means to insure that the shield 31 stays with the X-ray machine.

A plurality of sanitary disposable bags 23 are fabricated to encompass the radiation shield 31, as shown in FIG. 2, the plurality of disposable bags removably stored within a dispenser 21 of the disposable bags secured to an X-ray machine component for dispensing one of the plurality of disposable bags 23 for each patient being X-rayed and mounting the disposable bag over the shield for each use of the shield with a patient and for disposing of the disposable bag after each use of the shield with a patient to prevent the spread of contagious diseases between patients using the shield and from technicians handling the shield.

The radiation shield is made of a soft and flexible usually lead-impregnated radiation attenuation material designed to shield against all ionizing radiation exposure. The system of the present invention is designed to be securely mounted and conveniently stored on any mobile or stationary X-ray machine component. The radiation shield is permanently attached to a lengthy retractable and flexible cable of high strength material to prevent removal of the shield. The cable casing is preferably locked onto the X-ray unit component or mounted with a strong permanent adhesive or welded or otherwise permanently attached. The cable container holds the shield when not in use. The radiation shield is available in various sizes and thicknesses.

In use, the radiation shield attaching and covering system of the present invention is user friendly, reliable, and effective when used as intended. When placed in the impervious protective barrier, the radiation shield prevents the potential spread of infectious diseases caused by patient to patient or patient to technologist contact contamination. The radiation shield is removed from the protective barrier after the exposure and the barrier is discarded into the properly designated waste receptacle. Using the radiation shield attaching and covering system of the present invention will significantly improve patient satisfaction and confidence regarding radiation protection and infection control regardless of the patient's isolation precaution status. Real patient safety equals quality patient care. The system of the present invention is structured to meet all national and state regulatory, quality assurance, and accreditation readiness compliance.

It is understood that the preceding description is given merely by way of illustration and not in limitation of the invention and that various modifications may be made thereto without departing from the spirit of the invention as claimed.

SEQUENCE LISTING

Not Applicable.

What is claimed is:

1. A radiation shield securing and covering system comprising:

a radiation shield comprising a sheet of radiation attenuation material for preventing passage of all ionizing radiation through the shield to protect a patient from all ionizing radiation exposure on areas of the patient covered by the shield, the shield further comprising a means for handling the sheet of material during use with a patient and a means for hanging the material on an X-ray machine component;

a retractable cable attached at a first end by a means for permanently securing the cable to a radiation shield and at a second end to a retractable spool in a cable casing locked onto an X-ray machine component to insure that the shield is always with the X-ray machine to shield each patient being X-rayed from all ionizing radiation exposure on areas of the patient covered by the shield;

a plurality of sanitary disposable bags structured to encompass the radiation shield, the plurality of disposable bags removably stored within a dispenser of the disposable bags secured to an X-ray machine component for dispensing one of the plurality of disposable bags for each patient being X-rayed and mounting the disposable bag over the shield for each use of the shield with a patient and for disposing of the disposable bag after each use of the shield with a patient to prevent the spread of contagious diseases between patients using the shield and from technologists handling the shield.

2. The system of claim 1 further comprising at least one hook attached to the X-ray machine component and the means for handling the shield and means for hanging the shield comprises an opening adjacent to a top end of the shield to receive at least one hand of a user during use of the shield and alternately to receive the at least one hook for hanging the shield on the X-ray machine component.

3. The system of claim 2 wherein the at least one hook is attached to the cable casing.

4. The system of claim 3 wherein the opening comprises an elongated horizontal opening and the cable casing comprises a rigid structure having two hooks horizontally spaced on the casing to fit within the elongated horizontal opening to support the shield hanging on the hooks for storage of the shield.

5. The system of claim 1 wherein the cable casing houses a spring loaded spool to retract the cable after use of the shield.

6. The system of claim 1 wherein the cable casing further comprises a means for locking the cable casing onto the X-ray machine component.

* * * * *